US009808197B2

(12) United States Patent
Matsuno et al.

(10) Patent No.: US 9,808,197 B2
(45) Date of Patent: Nov. 7, 2017

(54) ELECTRONIC APPARATUS AND CONTROL METHOD

(71) Applicant: Kabushiki Kaisha Toshiba, Minato-ku, Tokyo (JP)

(72) Inventors: Takaya Matsuno, Tokyo (JP); Takashi Sudo, Tokyo (JP); Yasuhiro Kanishima, Tokyo (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 274 days.

(21) Appl. No.: 14/633,994

(22) Filed: Feb. 27, 2015

(65) Prior Publication Data
US 2016/0058374 A1    Mar. 3, 2016

(30) Foreign Application Priority Data

Aug. 27, 2014 (JP) ................. 2014-172409

(51) Int. Cl.
*A61B 5/1455* (2006.01)
*A61B 5/00* (2006.01)
*A61B 5/11* (2006.01)
*A61B 5/024* (2006.01)

(52) U.S. Cl.
CPC .......... *A61B 5/681* (2013.01); *A61B 5/02438* (2013.01); *A61B 5/14552* (2013.01); *A61B 5/7285* (2013.01); *A61B 5/02427* (2013.01); *A61B 5/11* (2013.01)

(58) Field of Classification Search
CPC ... A61B 5/0002; A61B 5/0059; A61B 5/1455; A61B 5/14551; A61B 5/14552; A61B 5/0205; A61B 5/72; A61B 5/721
See application file for complete search history.

(56) References Cited

U.S. PATENT DOCUMENTS 3,910,701 A * 10/1975 Henderson ........... G01N 21/255
                                                      600/322
5,203,329 A *  4/1993 Takatani ............ A61B 5/14552
                                                        356/41
6,402,690 B1 *  6/2002 Rhee .................... A61B 5/0002
                                                      600/323

(Continued)

FOREIGN PATENT DOCUMENTS

JP     2003-339678 A    12/2003
JP     2009-034427 A     2/2009

(Continued)

*Primary Examiner* — Eric Winakur
*Assistant Examiner* — Chu Chuan (JJ) Liu
(74) *Attorney, Agent, or Firm* — Knobbe, Martens Olson & Bear LLP

(57) ABSTRACT

According to one embodiment, a wearable electronic apparatus detects movement of a human body wearing the apparatus. The apparatus causes a first number of light emitters to emit light when a magnitude of the detected movement is less than a first value. The first number of light emitters is among a plurality of light emitters which emit light having different wavelengths, in which the light are received by a light receiver to obtain physiological information. The apparatus causes a second number greater than the first number of light emitters among the plurality of light emitters to emit light when the magnitude of the detected movement is greater than or equal to the first value.

6 Claims, 6 Drawing Sheets

(56) References Cited

U.S. PATENT DOCUMENTS

| | | | |
|---|---|---|---|
| 8,565,846 B2 | 10/2013 | Ono et al. | |
| 2004/0034293 A1* | 2/2004 | Kimball | A61B 5/14551 600/323 |
| 2009/0036762 A1 | 2/2009 | Tateda et al. | |
| 2011/0046462 A1 | 2/2011 | Ono et al. | |
| 2013/0217979 A1* | 8/2013 | Blackadar | A61B 5/14551 600/301 |

FOREIGN PATENT DOCUMENTS

| | | |
|---|---|---|
| JP | 2010-193949 A | 9/2010 |
| JP | 2013-150772 A | 8/2013 |
| WO | WO 2013/099509 A1 | 7/2013 |

\* cited by examiner

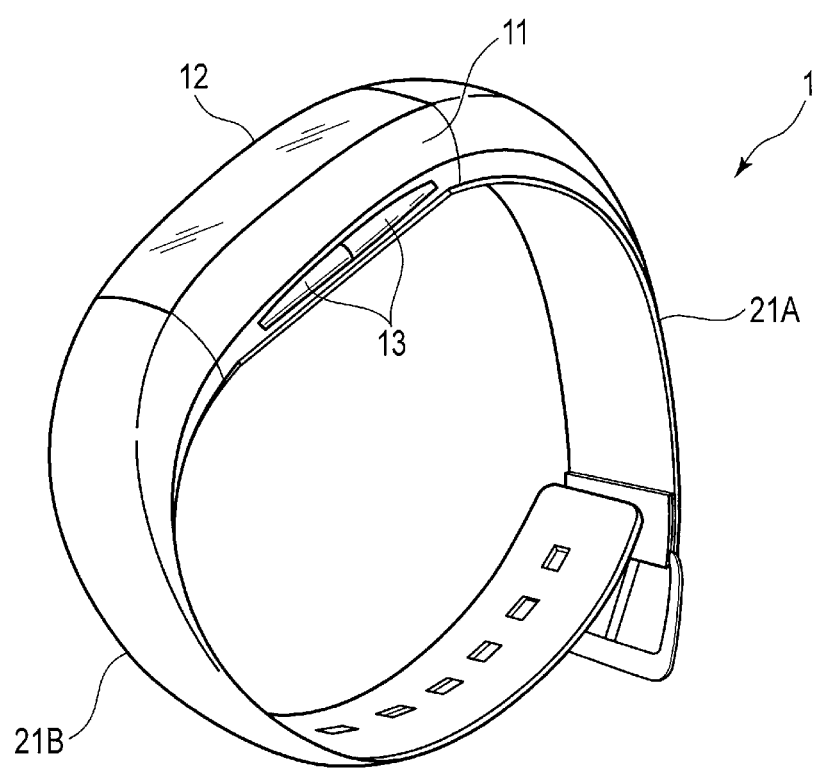
F I G. 1

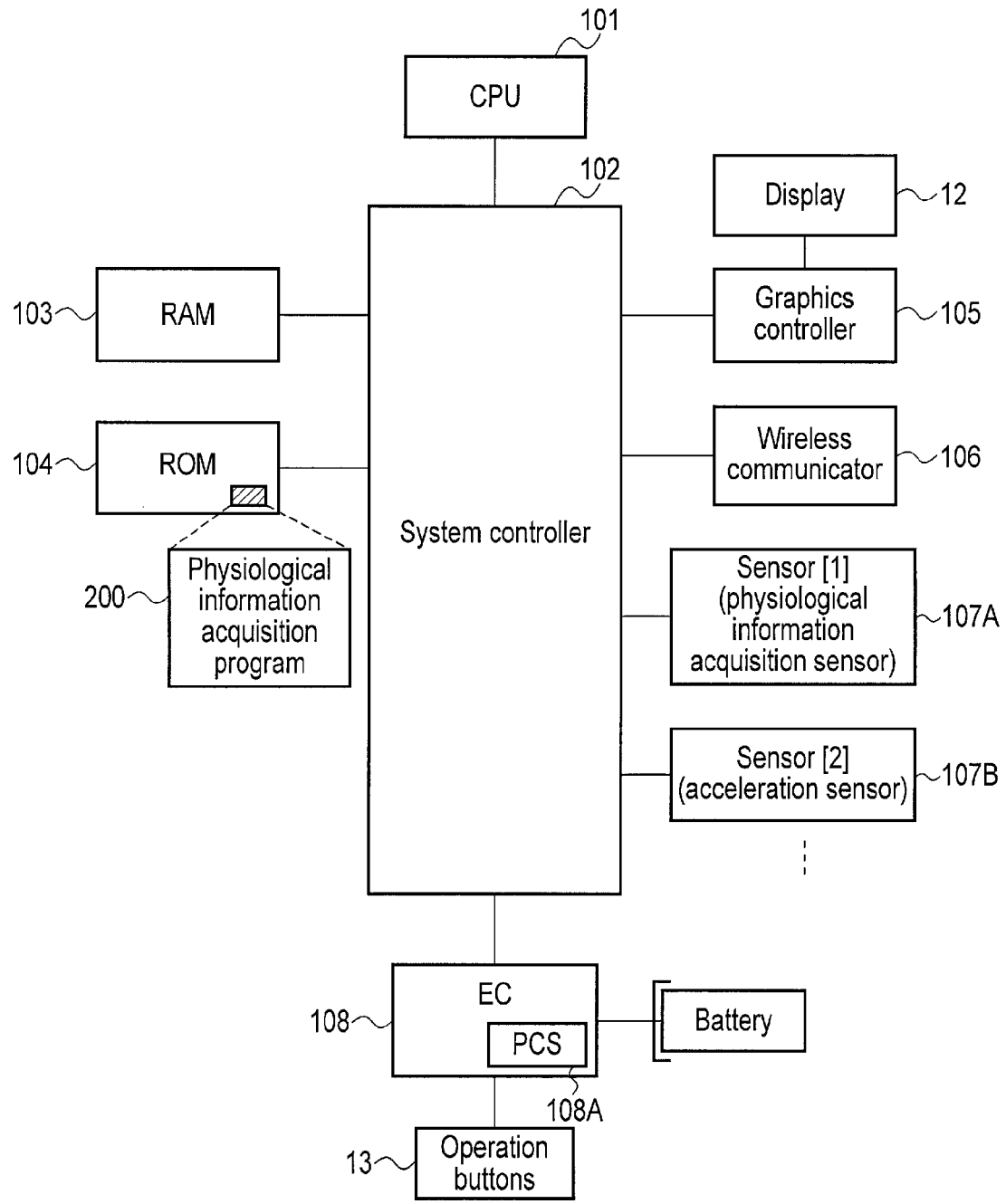
F I G. 2

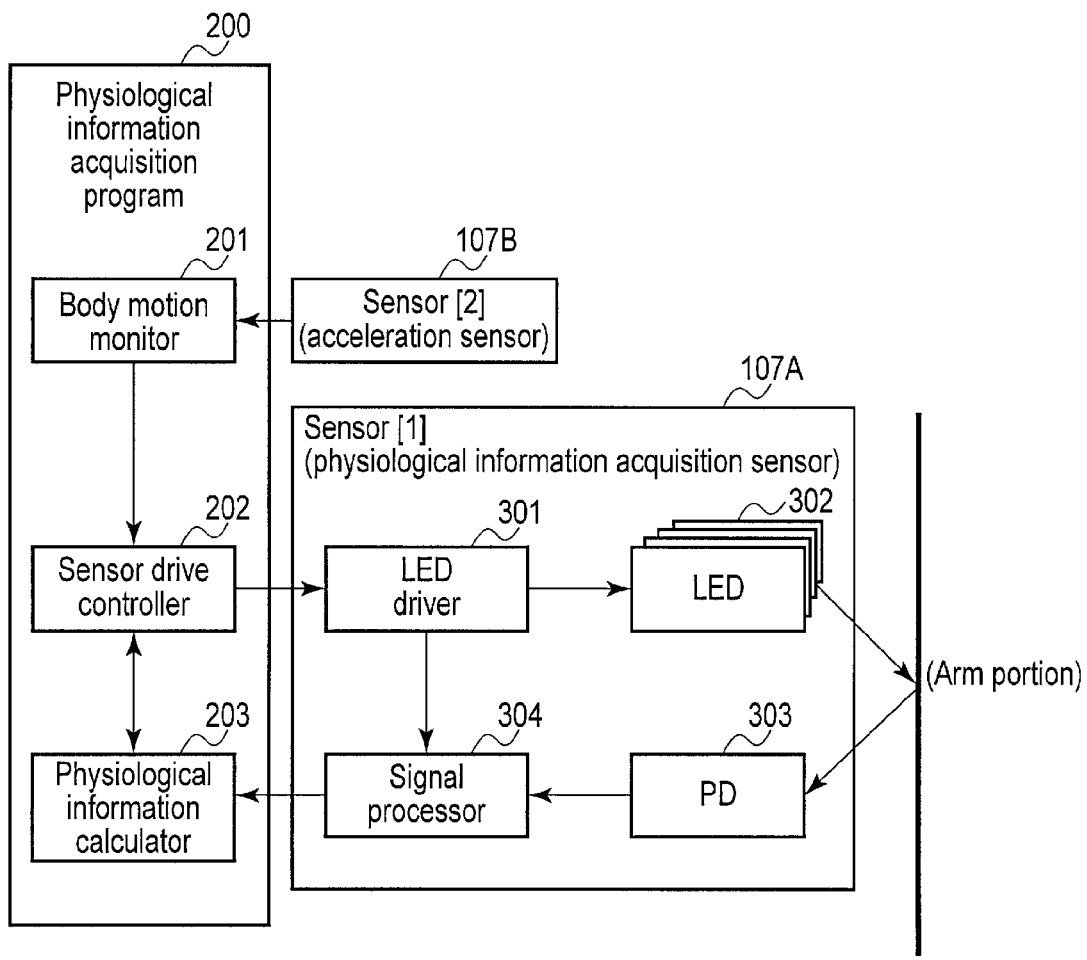
F I G. 4
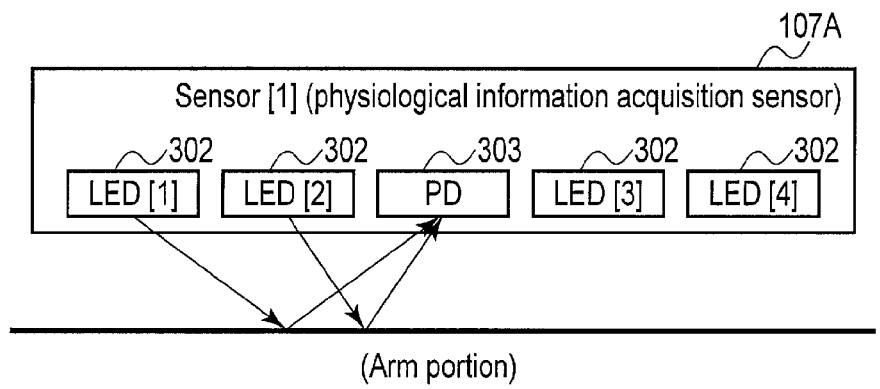
F I G. 5

ELECTRONIC APPARATUS AND CONTROL METHOD

CROSS-REFERENCE TO RELATED APPLICATIONS

This application is based upon and claims the benefit of priority from Japanese Patent Application No. 2014-172409, filed Aug. 27, 2014, the entire contents of which are incorporated herein by reference.

FIELD

Embodiments described herein relate generally to an electronic apparatus and a control method.

BACKGROUND

Recently, electronic apparatuses which can be powered by battery and carried easily, such as tablet computers and smartphones, have become widespread. At the same time, electronic apparatuses of the type which are worn on a human body in the form of, for example, wristwatch and glasses, which are referred to as wearable devices, etc., have been developed. Some of these wearable devices can obtain physiological information on a user wearing the wearable device, such as a pulse and percutaneous arterial blood oxygen saturation ($S_pO_2$).

As a method of acquiring the physiological information such as the pulse and $S_pO_2$, a method of irradiating light onto the human body and analyzing the light which has been reflected from or has passed through the body is known. This method uses a difference in absorptivity of the light beams of specific wavelengths (typically, red light and infrared light) between oxyhemoglobin and deoxyhemoglobin in the blood.

A device which acquires the physiological information by this method is easily affected by movement of the human body (which may be hereinafter referred to as body motion), and accuracy of the physiological information which is acquired in a state where the body motion is large is decreased. As countermeasures against body motion, one idea is to irradiate light beams of many more different wavelengths onto the human body in order to acquire the physiological information accurately even in a situation where the body motion is large.

Meanwhile, the wearable device is required to be small and light in terms of the feature that it is worn on the human body, and the battery capacity for supplying operating power is also limited. Accordingly, achieving low power consumption in the wearable device is strongly required.

BRIEF DESCRIPTION OF THE DRAWINGS

A general architecture that implements the various features of the embodiments will now be described with reference to the drawings. The drawings and the associated descriptions are provided to illustrate the embodiments and not to limit the scope of the invention.

FIG. 1 is an exemplary view showing an appearance of an electronic apparatus of an embodiment.

FIG. 2 is an exemplary diagram showing a system configuration of the electronic apparatus of the embodiment.

FIG. 4 is an exemplary diagram showing functional blocks regarding acquisition of the physiological information by the electronic apparatus of the embodiment.

FIG. 5 is an exemplary illustration showing an example of a mode of operation at normal times of a physiological information acquisition sensor 107A which is mounted on the electronic apparatus of the embodiment.

DETAILED DESCRIPTION

Figure 3:
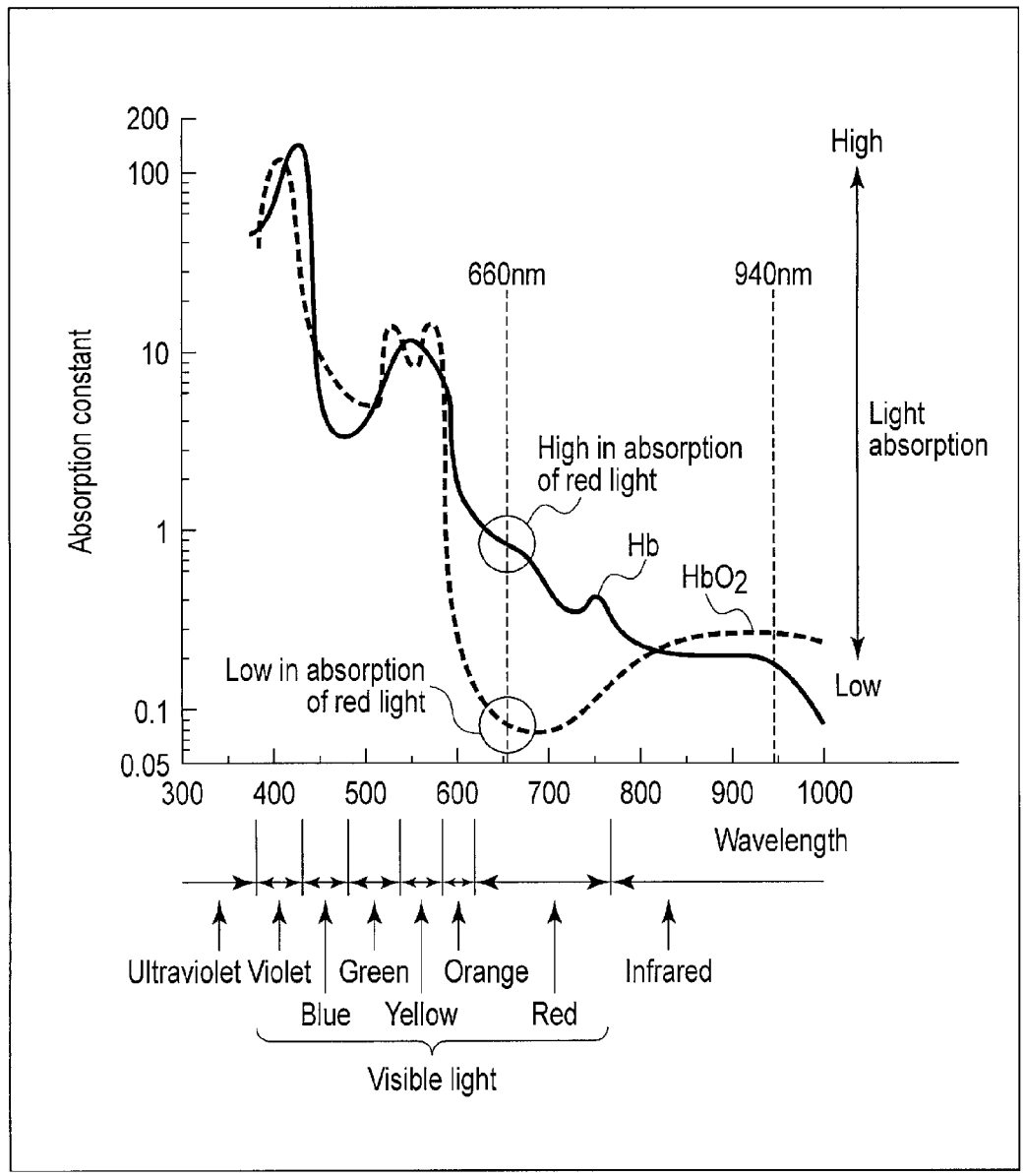
FIG. 3 is an exemplary illustration for explaining a principle of acquiring physiological information by a physiological information acquisition program which operates on the electronic apparatus of the embodiment.

Various embodiments will be described hereinafter with reference to the accompanying drawings.

In general, according to one embodiment, a wearable electronic apparatus comprises a plurality of light emitters, a light receiver, an acquisition processor, a sensor and a controller. The plurality of light emitters emit light having different wavelengths. The light receiver receives reflected light or transmitted light emitted from the light emitters. The reflected light is from a human body wearing the apparatus. The transmitted light is passing through the human body. The acquisition processor acquires physiological information on the human body wearing the apparatus based on the reflected light or the transmitted light received by the light receiver. The sensor detects movement of the human body wearing the apparatus. The controller causes a first number of the light emitters to emit light when a magnitude of the movement detected by the sensor is less than a first value, and causes a second number greater than the first number of the light emitters to emit light when the magnitude of the movement detected by the sensor is greater than or equal to the first value. The light emitter of the second number comprises the light emitter of the first number.

An electronic apparatus of the present embodiment is realized as a wearable device, which is of the type worn on a human body. Here, it is assumed that the present electronic apparatus is realized as a wristwatch-type wearable device, and worn on an arm portion (wrist) of a user.

FIG. 1 is an exemplary perspective view of a wearable device 1. The wearable device 1 comprises a main body 11. Various electronic components are provided in the main body 11. On an upper surface of the main body 11, a display 12 such as a liquid crystal display (LCD) is provided. The display 12 may be a touchscreen display capable of detecting contact on its display screen by a finger or the like. Also, on a side surface of the main body 11, operation buttons 13 are provided.

The wearable device 1 comprises belts (bands) 21A and 21B for wearing the main body 11 on the human body (arm portion). Each of the belts 21A and 21B is realized by a member having flexibility.

FIG. 2 is an exemplary diagram showing a system configuration of the wearable device 1.

Apart from the display 12 and the operation buttons 13 shown in FIG. 1, in the main body 11 of the wearable device 1, a CPU 101, a system controller 102, a RAM 103, a ROM 104, a graphics controller 105, a wireless communicator 106, sensors 107A, 107B, . . . , an embedded controller (EC) 108, etc., are arranged, as shown in FIG. 2.

The CPU 101 is a processor for controlling the operation of the various components in the wearable device 1. The CPU 101 executes various programs stored in the ROM 104 while utilizing the RAM 103 as a work area. As one of the various programs, a physiological information acquisition program 200 which will be described later exists.

The system controller 102 is a device connecting between a local bus of the CPU 101 and the various components. In the system controller 102, various controllers for driving and controlling the various components, such as a memory controller for managing access control of the RAM 103 and the ROM 104, are incorporated.

The graphics controller 105 is a display controller for controlling the display 12. The display 12 displays a screen image based on a display signal generated by the graphics controller 105.

The wireless communicator 106 is a module which executes wireless communication conforming to the IEEE 802.11 standard, for example. The sensors 107A, 107B, . . . are, for example, a physiological information acquisition sensor, an acceleration sensor, an ambient light sensor, a temperature sensor, a humidity sensor, and a magnetic field sensor. It is assumed here that the sensor 107A is the physiological information acquisition sensor, and the sensor 107B is a triaxial acceleration sensor. A detected value of each of the sensors is used in the various programs including the physiological information acquisition program 200 by way of a register in the system controller 102.

The EC 108 is a single-chip microcomputer including a power supply controller (PSC) 108A which manages control of supply of the operating power for the various components in the wearable device 1. The EC 108 comprises the function of accepting an instruction from the user by an operation of the operation buttons 13.

The physiological information acquisition program 200 is a program for acquiring physiological information such as a pulse and $S_pO_2$ of the user wearing the wearable device 1 by using the physiological information acquisition sensor 107A. The physiological information acquisition sensor 107A is a reflective photoelectric sensor, for example. The physiological information acquisition sensor 107A irradiates light of a specific wavelength toward the human body (arm portion) and also receives the reflected light (i.e., the light reflected from the human body (arm portion)). The physiological information acquisition program 200 utilizes the phenomenon that light is absorbed by hemoglobin in the blood and analyzes the reflected light received by the physiological information acquisition sensor 107A, thereby calculating the pulse and $S_pO_2$ of the user. Note that when the physiological information acquisition sensor 107A is a transmissive photoelectric sensor, it receives the light which has passed through the human body (arm portion).

Now, referring to FIG. 3, a principle of the physiological information acquisition program 200 acquiring the physiological information from the detected value of the physiological information acquisition sensor 107A will be briefly described.

Hemoglobin which transports oxygen exists in the blood. Hemoglobin has the feature of showing a difference in absorptivity when the hemoglobin is bound to oxygen and when it is not bound to oxygen. Hemoglobin which is not bound to oxygen is called, for example, deoxyhemoglobin [Hb], and hemoglobin which is bound to oxygen is called oxyhemoglobin [HbO$_2$].

For example, the deoxyhemoglobin [Hb] absorbs more red light (i.e., light having a wavelength of 660 nm, for example) than the oxyhemoglobin [HbO$_2$]. Conversely, the deoxyhemoglobin [Hb] absorbs less infrared light (i.e., light having a wavelength of 940 nm, for example) than the oxyhemoglobin [HbO$_2$]. Thus, for example, the physiological information acquisition sensor 107A is made to emit red light and infrared light, and receive the reflected light. Then, based on the amount of reflected red light and infrared light, the physiological information acquisition program 200 calculates the pulse, the $S_pO_2$, etc. While the wavelengths of 660 nm and 940 nm were described above as an example, light having other wavelengths also exhibits a difference in the absorptivity of the irradiated light between the deoxyhemoglobin [Hb] and the oxyhemoglobin [HbO$_2$], as shown in FIG. 3.

It should be noted that the accuracy of the physiological information acquired by the physiological information acquisition program 200 from the detected value of the physiological information acquisition sensor 107A is greatly decreased when the movement of the user wearing the wearable device 1, that is, the body motion, is large. This is because a distance between the physiological information acquisition sensor 107A and the human body (arm portion) varies. In order to increase the accuracy of the physiological information to be obtained even in a situation where the body motion is large, instead of calculating the physiological information with light beams having two different wavelengths, one solution is to use a light beam of another wavelength and calculate the physiological information with light beams having three or more different wavelengths.

However, the amount of power consumed by the physiological information acquisition sensor 107A which emits light relative to the total amount of power consumption of the wearable device 1 is quite large. Accordingly, it is not desirable to simply increase the number of types of light to be emitted. Thus, the wearable device 1 of the present embodiment is structured such that it can acquire the physiological information accurately even if the body motion is large while suppressing the increase in the power consumption. This point will be hereinafter described in detail.

FIG. 4 is an exemplary diagram showing functional blocks regarding acquisition of the physiological information by the wearable device 1.

As shown in FIG. 4, the physiological information acquisition program 200 comprises a body motion monitor 201, a sensor drive controller 202, and a physiological information calculator 203.

The body motion monitor 201 performs monitoring to check whether movement (body motion) of the user wearing the wearable device 1 is over a threshold based on the detected value of the acceleration sensor 107B. When the body motion is greater than or equal to the threshold, the body motion monitor 201 notifies this information to the sensor drive controller 202.

While it has been described that the body motion is monitored by the acceleration sensor, based on the assumption that space is formed between the wearable device 1 and the arm portion of the user by the body motion, for example, the body motion may be monitored by an ambient light sensor. Other than the above, various sensors can be used for monitoring the body motion, and a plurality of sensors may also be used.

The sensor drive controller 202 manages drive control of the physiological information acquisition sensor 107A. As shown in FIG. 4, the physiological information acquisition sensor 107A comprises a light-emitting diode (LED) driver 301, a plurality of LEDs 302, a photo diode (PD) 303, and a signal processor 304. As the LEDs 302, it is assumed here that a total of four LEDs, that is, an LED [1] which emits red light (i.e., light having a wavelength of 660 nm, for example), an LED [2] which emits infrared light (i.e., light having a wavelength of 940 nm, for example), and two more LEDs [3, 4] which are different from the aforementioned two LEDs and emit light beams having wavelengths different from each other, exist. As regards the two LEDs [3, 4] mentioned at the end, one of them should preferably emit light having a wavelength which is absorbed more by the deoxyhemoglobin [Hb] than the oxyhemoglobin [HbO$_2$], and the other one should preferably emit light having a wavelength which is absorbed more by the oxyhemoglobin [HbO$_2$] than the deoxyhemoglobin [Hb]. These LEDs 302 and the PD 303 are arranged on a rear surface of the main body 11 which is close to the skin of the arm portion of the user wearing the wearable device 1.

The LED driver 301 drives the LEDs 302. The LED driver 301 can vary the number of LEDs 302 which should emit light in accordance with an instruction from the sensor drive controller 202 (of the physiological information acquisition program 200). Also, the LED driver 301 supplies a synchronous signal indicating light-emission timing of the LEDs 302 to the signal processor 304.

The PD 303 receives the reflected part of light emitted from the LEDs 302, and outputs a signal indicating the amount of light received. The signal processor 304 is a module which performs processing, such as amplification and filtering, for the signal output from the PD 303. Based on the synchronous signal from the LED driver 301, the signal processor 304 outputs a detected value, which is generated by performing the aforementioned processing for the signal output from the PD 303 at the light-receiving timing of the PD 303 corresponding to the light-emission timing of the LEDs 302, to the physiological information calculator 203 (of the physiological information acquisition program 200).

Normally, the sensor drive controller 202 instructs the LED driver 301 (of the physiological information acquisition sensor 107A) to cause the LED [1] which emits red light (i.e., light having a wavelength of 660 nm, for example) and the LED [2] which emits infrared light (i.e., light having a wavelength of 940 nm, for example) of the four LEDs 302 to emit light. In this way, as shown in FIG. 5, the physiological information acquisition sensor 107A irradiates light beams of two different wavelengths onto the arm portion of the user by the two LEDs 302, receives the reflected light by the PD 303, and outputs the detected value indicating the amount of light received.

Figure 6:
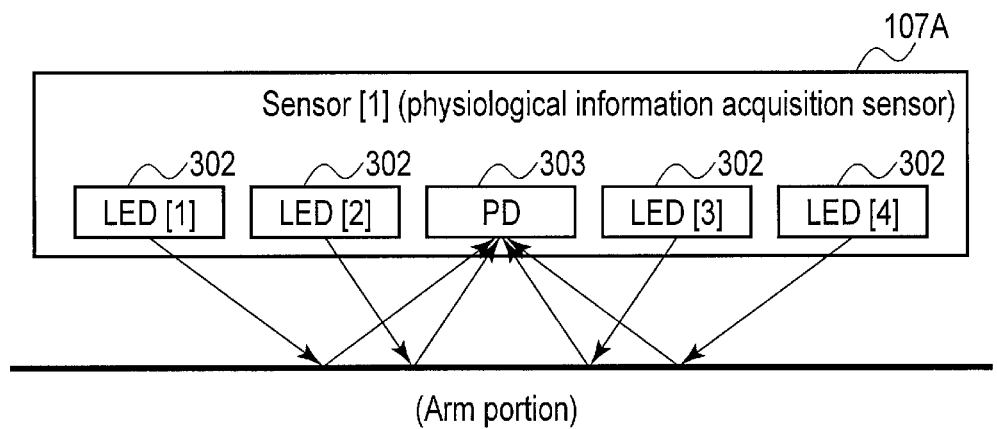
FIG. 6 is an exemplary illustration showing an example of a mode of operation when body motion detected by the physiological information acquisition sensor 107A which is mounted on the electronic apparatus of the embodiment is greater than or equal to a threshold.

Also, as described above, when the body motion is greater than or equal to the threshold, the body motion monitor 201 notifies this information to the sensor drive controller 202. Under the circumstances, when this notification is received, the sensor drive controller 202 instructs the LED driver 301 (of the physiological information acquisition sensor 107A) to cause all four LEDs 302 to emit light. In this way, as shown in FIG. 6, the physiological information acquisition sensor 107A irradiates light beams of four different wavelengths onto the arm portion of the user by the four LEDs 302, receives the reflected light by the PD 303, and outputs the detected value indicating the amount of light received.

As can be seen, the wearable device 1 realizes acquisition of physiological information with high precision by adaptively switching the wavelength to be used depending on the situation of the body motion. In addition, the wearable device 1 can prevent an increase in the power consumption by not always using multiple wavelengths but using them only when necessary.

Figure 7:
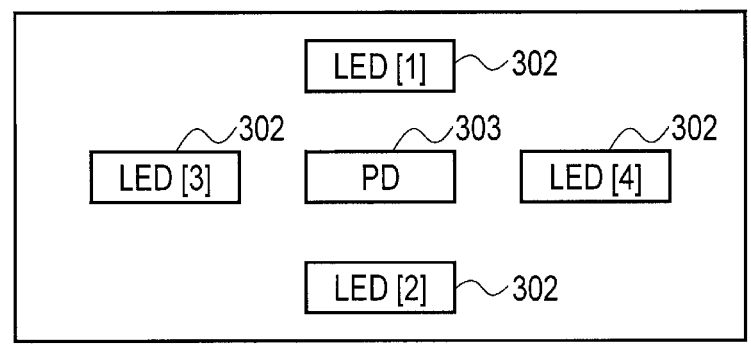
FIG. 7 is an exemplary illustration showing an example of arrangement of a plurality of LEDs in the physiological information acquisition sensor 107A which is mounted on the electronic apparatus of the embodiment.

Preferably, the LEDs 302 should be arranged such that paths of light beams emitted from the LEDs 302, respectively, to the PD 303 are substantially equidistant. More specifically, as shown in FIG. 7, for example, the LEDs 302 should preferably be arranged circumferentially about the PD 303.

Figure 8:
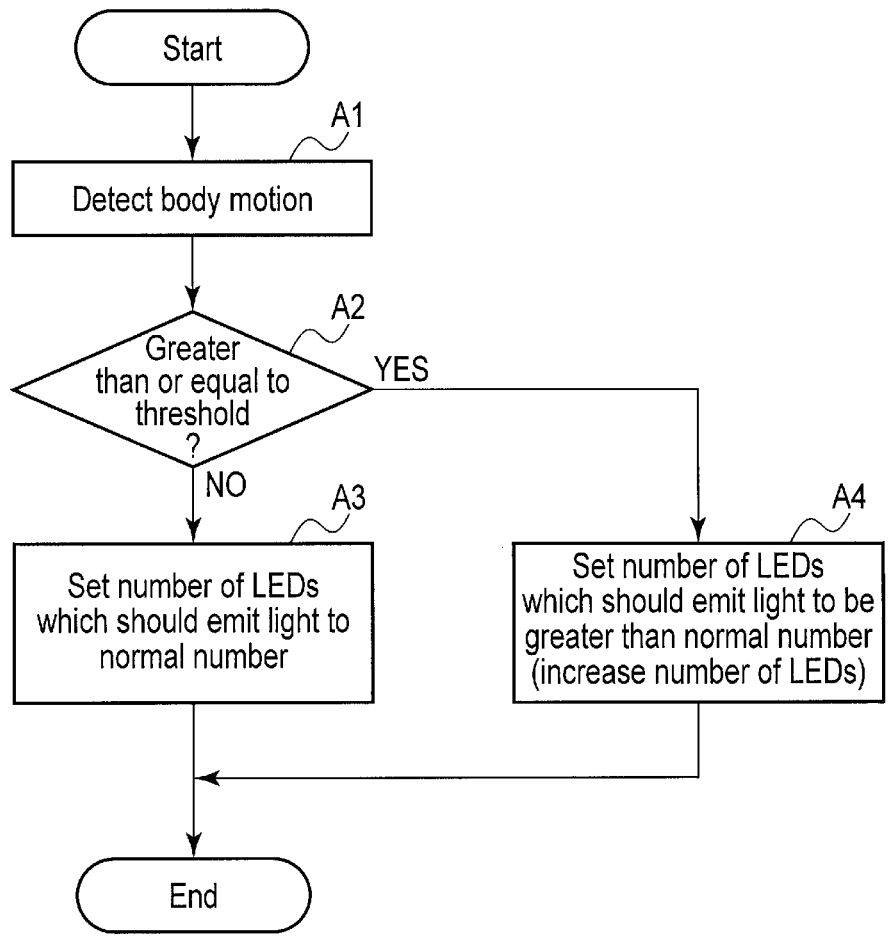
FIG. 8 is an exemplary flowchart showing processing procedures in acquiring the physiological information by the electronic apparatus of the embodiment.

FIG. 8 is an exemplary flowchart showing processing procedures in acquiring the physiological information by the wearable device 1.

In acquiring the physiological information, the wearable device 1 detects body motion (block A1). When the body motion which has been detected is below a threshold (NO in block A2), the wearable device 1 sets the number of LEDs which should emit light to a normal number (block A3). On the other hand, when the body motion which has been detected is greater than or equal to the threshold (YES in block A2), the wearable device 1 sets the number of LEDs which should emit light to a number greater than the normal number (block A3).

As described above, the wearable device 1 of the present embodiment realizes acquisition of the physiological information accurately even if the body motion is large while suppressing the increase in the power consumption.

Further, in the above description, an example of switching the wavelengths of the light to be used for obtaining the physiological information in two stages in the case where the body motion is less than a threshold and in the case where the body motion is greater than or equal to the threshold was given. The wavelengths of the light to be used may be switched in a plurality of stages of not less than three in accordance with the magnitude of the body motion.

Since various types of processing of the present embodiment can be realized by a computer program, it is possible to easily realize an advantage similar to that of the present embodiment by simply installing a computer program on an ordinary computer by way of a computer-readable storage medium containing the computer program, and executing this computer program.

The various modules of the systems described herein can be implemented as software applications, hardware and/or software modules, or components on one or more computers, such as servers. While the various modules are illustrated separately, they may share some or all of the same underlying logic or code.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A wearable electronic apparatus, comprising:
   a plurality of light emitters including a first LED, a second LED, a third LED and a fourth LED, the first LED emitting red light, the second LED emitting infrared light, the third LED and the fourth LED emitting light different from the light emitted by the first LED and the second LED, and having wavelengths different from each other;

a light receiver to receive reflected light or transmitted light emitted from the light emitters, the reflected light from a human body wearing the apparatus, the transmitted light passing through the human body;

a sensor to detect movement of the human body wearing the apparatus; and a CPU configured to execute various programs including a physiological information acquisition program, wherein the CPU is configured to:

two light emitters including the first LED which emits red light and the second LED which emits infrared light to emit light when the magnitude of the movement detected by the sensor is less than a threshold value, and acquire physiological information of the human body based on an output signal from the light receiver which receives the reflected light or the transmitted light; and;

cause four light emitters including the first LED which emits red light, the second LED which emits infrared light, and the third LED and the fourth LED which emit light different from the light emitted by the first LED and the second LED, and having wavelengths different from each other to emit light when the magnitude of the movement detected by the sensor is greater than or equal to the threshold value, and acquire the physiological information of the human body based on an output signal from the light receiver which receives the reflected light or the transmitted light.

2. The apparatus of claim 1, wherein the first LED, the second LED, the third LED and the fourth LED are arranged such that paths of the light emitted from the plurality of light emitters to the light receiver are equidistant.

3. The apparatus of claim 2, wherein the first LED, the second LED, the third LED and the fourth LED are arranged on a circumference of the light receiver.

4. The apparatus of claim 1, wherein the third LED emits light having a wavelength which deoxyhemoglobin [Hb] absorbs more strongly than oxyhemoglobin [$HbO_2$], and the fourth LED emits light having a wavelength which oxyhemoglobin [$HbO_2$] absorbs more strongly than deoxyhemoglobin [Hb].

5. The apparatus of claim 1, wherein the light receiver is configured to output the output signal in accordance with a synchronous signal indicative of light-emission timing of the plurality of light emitters.

6. A method of controlling a wearable electronic apparatus, the method comprising:

detecting, by a sensor, movement of a human body wearing the apparatus;

causing two light emitters including a first LED which emits red light and a second LED which emits infrared light to emit light when the magnitude of the movement detected by the sensor is less than a threshold value, and acquiring physiological information of the human body based on an output signal from a light receiver which receives reflected light or transmitted light; and causing four light emitters including the first LED which emits red light, the second LED which emits infrared light, and the third LED and the fourth LED which emit light different from the light emitted by the first LED and the second LED, and having wavelengths different from each other to emit light when the magnitude of the movement detected by the sensor is greater than or equal to the threshold value, and acquiring the physiological information of the human body based on an output signal from the light receiver which receives the reflected light or the transmitted light.

* * * * *